(12) United States Patent
Carter et al.

(10) Patent No.: US 8,084,002 B2
(45) Date of Patent: Dec. 27, 2011

(54) CHEMICAL SENSING DEVICE

(75) Inventors: Timothy Joseph Nicholas Carter, Sittingbourne (GB); Steven Andrew Ross, Sittingbourne (GB)

(73) Assignee: Vivacta Ltd., Sittingbourne, Kent (GB)

( * ) Notice: Subject to any disclaimer, the term of this patent is extended or adjusted under 35 U.S.C. 154(b) by 325 days.

(21) Appl. No.: 12/299,983

(22) PCT Filed: May 4, 2007

(86) PCT No.: PCT/GB2007/001648
§ 371 (c)(1),
(2), (4) Date: Nov. 7, 2008

(87) PCT Pub. No.: WO2007/129064
PCT Pub. Date: Nov. 15, 2007

(65) Prior Publication Data
US 2009/0123962 A1 May 14, 2009

(30) Foreign Application Priority Data
May 8, 2006 (GB) .................................. 0609060.9

(51) Int. Cl.
G01N 25/20 (2006.01)
G01N 27/00 (2006.01)

(52) U.S. Cl. ..... 422/402; 422/403; 422/430; 422/82.01; 422/82.05; 436/147; 436/149

(58) Field of Classification Search .................. 422/402, 422/430, 82.01, 82.05; 436/147, 149
See application file for complete search history.

(56) References Cited

U.S. PATENT DOCUMENTS

| 5,622,868 | A | * | 4/1997 | Clarke et al. ................... 436/147 |
| 2002/0146345 | A1 | | 10/2002 | Neilson et al. |
| 2004/0141879 | A1 | | 7/2004 | Loomis et al. |
| 2005/0196322 | A1 | * | 9/2005 | Truex et al. ................. 422/82.01 |

FOREIGN PATENT DOCUMENTS

| EP | 0435245 A3 | 7/1991 |
| JP | 56168144 A | 12/1981 |
| JP | 2005326269 A | 11/2005 |
| WO | 8605275 A1 | 9/1986 |
| WO | 9013017 A1 | 11/1990 |
| WO | 2004090512 A1 | 10/2004 |
| WO | 2006079795 A1 | 8/2006 |

OTHER PUBLICATIONS

Search Report from GB Patent Office for GB0609060.9, dated Sep. 15, 2006.

* cited by examiner

*Primary Examiner* — Lyle Alexander
(74) *Attorney, Agent, or Firm* — Rothwell, Figg, Ernst & Manbeck, pc

(57) ABSTRACT

The present application relates to a chemical sensing device for detecting an analyte in a liquid sample containing suspended particles. The device comprises a radiation source adapted to generate electromagnetic radiation, a transducer (3) having a pyroelectric or piezoelectric element and electrodes which is capable of transducing a change in energy to an electrical signal, at least one reagent (2) on or proximal to the transducer (3), the reagent being capable of absorbing the electromagnetic radiation to generate energy when in contact with the analyte, a chamber (9) for holding the sample in fluid contact with transducer, and a detector which is capable of detecting the electrical signal generated by the transducer. The transducer is in a plane from +45° to −45° to the vertical.

14 Claims, 4 Drawing Sheets

CHEMICAL SENSING DEVICE

This application is a filing under 35 USC 371 of PCT/GB2007/001648, filed May 4, 2007, which claims priority from GB 0609060.9, filed May 8, 2006. These prior applications are incorporated herein by reference.

The present invention relates to a chemical sensing device and in particular to a chemical sensing device employing a transducer.

The monitoring of analytes in solution, such as biologically important compounds in bioassays, has a broad applicability. Accordingly, a wide variety of analytical and diagnostic devices are available. Many devices employ a reagent which undergoes an eye-detectable colour change in the presence of the species being detected. The reagent is often carried on a test strip and optics may be provided to assist in the measurement of the colour change.

WO 90/13017 discloses a pyroelectric or other thermoelectric transducer element in a strip form. Thin film electrodes are provided and one or more reagents are deposited on the transducer surface. The reagent undergoes a selective calorimetric change when it comes into contact with the species being detected. The device is then typically inserted into a detector where the transducer is illuminated usually from below by an LED light source and light absorption by the reagent is detected as microscopic heating at the transducer surface. The electrical signal output from the transducer is processed to derive the concentration of the species being detected.

The system of WO 90/13017 provides for the analysis of species which produce a colour change in the reagent on reaction or combination with the reagent. For example, reagents include pH and heavy metal indicator dyes, reagents (e.g. o-cresol in ammoniacal copper solution) for detecting aminophenol in a paracetamol assay, and a tetrazolium dye for detecting an oxidoreductase enzyme in an enzyme-linked immuno-sorbant assay (ELISA). However, while this system is useful in certain applications, it has been considered suitable only for analysis where the species being analysed generates a colour change in the reagent since it is the reagent which is located on the surface of the transducer. Therefore, this system cannot be applied to the analysis of species which do not cause a colour change in the reagent or when the colour change is not on the surface of the transducer. In the field of bioassays, this gives the system limited applicability.

WO 2004/090512 discloses a device based on the technology disclosed in WO 90/13017, but relies on the finding that energy generated by non-radiative decay in a reagent on irradiation with electromagnetic radiation may be detected by a transducer even when the reagent is not in contact with the transducer, and that the time delay between the irradiation with electromagnetic radiation and the electrical signal produced by the transducer is a function of the distance of the reagent from the surface of the film. This finding provided a device capable of "depth profiling" which allows the device to distinguish between an analyte bound to the surface of the transducer and an analyte in the bulk liquid. This application therefore discloses a device which is able to be used in assays, typically bioassays, without having to carry out a separate washing step between carrying out a binding event and detecting the results of that event.

The devices disclosed in WO 90/13017 and WO 2004/090512 have found wide applicability but the applicability is limited when the device is used to detect the presence of an analyte in a sample which contains suspended particles, such as whole blood containing suspended red blood cells (i.e. uncoagulated blood containing cells), suspended samples of foodstuffs or heavy metals in a water sample contaminated with suspended particles.

There remains a requirement in the art, therefore, for a system which can operate in the presence of a sample which contains suspended particles. This is particularly important since many assays are performed on analytes present in such samples.

Accordingly, the present invention provides a device for detecting an analyte in a liquid sample containing suspended particles comprising a radiation source adapted to generate electromagnetic radiation, a transducer having a pyroelectric or piezoelectric element and electrodes which is capable of transducing a change in energy to an electrical signal, at least one reagent on or proximal to the transducer, the reagent being capable of absorbing the electromagnetic radiation to generate energy when in contact with the analyte, a chamber for holding the sample in fluid contact with transducer, and a detector which is capable of detecting the electrical signal generated by the transducer, wherein the transducer is in a plane from +45° to −45° to the vertical.

The present invention also provides a method for detecting an analyte in a liquid sample containing suspended particles comprising introducing a sample containing suspended particles into the chamber of the device as defined herein, irradiating the sample with electromagnetic radiation, and detecting the electrical signal generated by the transducer.

This device/method allows the user to detect the presence of an analyte in a sample containing suspended particles which may settle under the influence of gravity.

The present invention will now be described with reference to the drawings, in which FIG. 1 shows a schematic representation of the chemical sensing device of the present invention;

Figure 1:
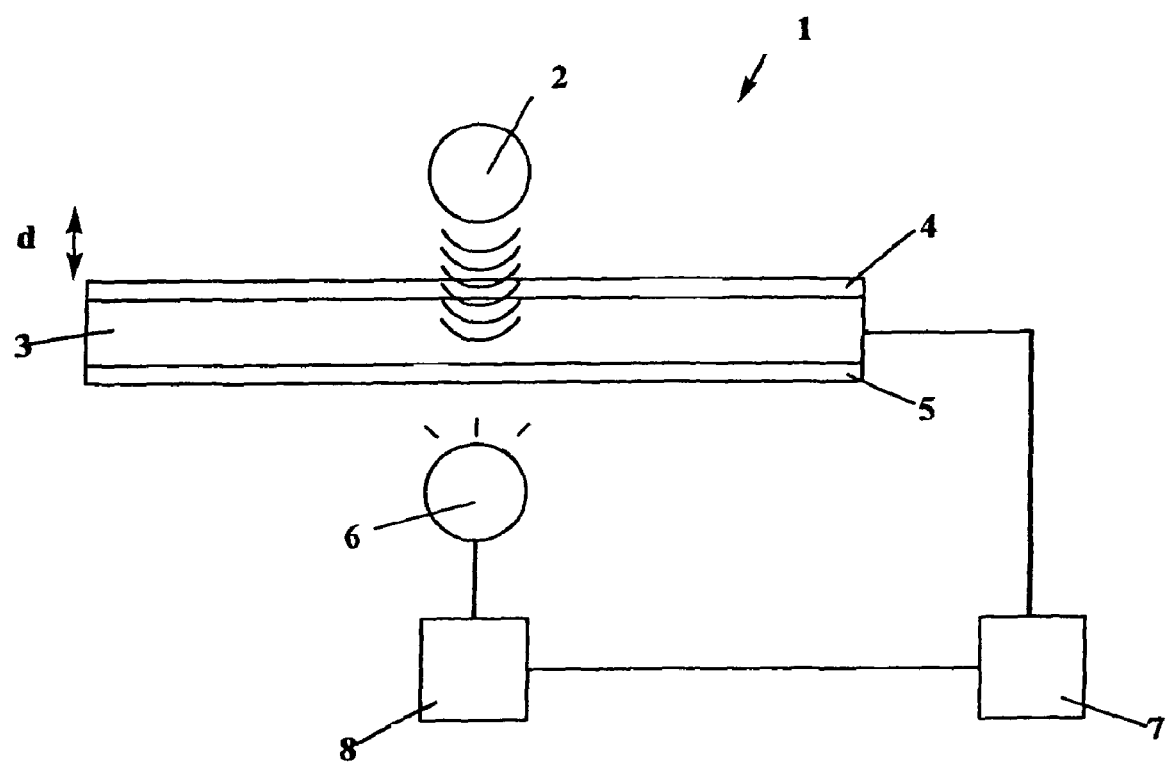

FIG. 1 shows the principle of the chemical sensing device 1 of the present invention. The device 1 relies on heat generation in a reagent 2 on irradiation of the reagent 2 with electromagnetic radiation. The device 1 comprises a pyroelectric or piezoelectric transducer 3 having electrode coatings 4,5. The transducer 3 is preferably a poled polyvinylidene fluoride film. The electrode coatings 4,5 are preferably formed from indium tin oxide having a thickness of about 35 nm, although almost any thickness is possible from a lower limit of 1 nm below which the electrical conductivity is too low and an upper limit of 100 nm above which the optical transmission is too low (it should not be less than 95% T). A reagent 2 is held on or proximal to the transducer 3 using any suitable technique, shown here attached to the upper electrode coating 4. The reagent may be in any suitable form and a plurality of reagents may be deposited. Preferably, the reagent 2 is adsorbed on to the upper electrode, e.g. covalently coupled or bound via intermolecular forces such as ionic bonds, hydrogen bonding or van der Waal's forces. A key feature of this device is that the reagent 2 generates heat when irradiated by a source of electromagnetic radiation 6, such as light, preferably visible light. The light source may be, for example, an LED. The light source 6 illuminates the reagent 2 with light of the appropriate wavelength (e.g. a complementary colour). Although not wishing to be bound by theory, it is believed that the reagent 2 absorbs the light to generate an excited state which then undergoes non-radiative decay thereby generating energy, indicated by the curved lines in FIG. 1. This energy is primarily in the form of heat (i.e. thermal motion in the environment) although other forms of energy, e.g. a shock wave, may also be generated. The energy is, however, detected by the transducer and converted into an electrical signal. The device of the present invention is calibrated for the particular reagent being measured and hence the precise form of the energy generated by the non-radiative decay does not need to be determined. Unless otherwise specified the term "heat" is used herein to mean the energy generated by non-radiative decay. The light source 6 is positioned so as to illuminate the reagent 2. Preferably, the light source 6 is positioned substantially perpendicular to the transducer 3 and electrodes 4,5 and the reagent 2 is illuminated through the transducer 3 and electrodes 4,5. The light source may be an internal light source within the transducer in which the light source is a guided wave system. The wave guide may be the transducer itself or the wave guide may be an additional layer attached to the transducer. Preferably a wavelength of 525 nm is used.

The energy generated by the reagent 2 is detected by the transducer 3 and converted into an electrical signal. The electrical signal is detected by a detector 7. The light source 6 and the detector 7 are both under the control of the controller 8.

In one embodiment of the present invention, the light source 6 generates a series of pulses of light (the term "light" used herein means any form of electromagnetic radiation unless a specific wavelength is mentioned) which is termed "chopped light". In principle, a single flash of light, i.e. one pulse of electromagnetic radiation, would suffice to generate a signal from the transducer 3. However, in order to obtain a reproducible signal, a plurality of flashes of light are used which in practice requires chopped light. The frequency at which the pulses of electromagnetic radiation are applied may be varied. At the lower limit, the time delay between the pulses must be sufficient for the time delay between each pulse and the generation of an electrical signal to be determined. At the upper limit, the time delay between each pulse must not be so large that the period taken to record the data becomes unreasonably extended. Preferably, the frequency of the pulses is from 2-50 Hz, more preferably 5-15 Hz and most preferably 10 Hz. This corresponds to a time delay between pulses of 20-500 ms, 66-200 ms and 100 ms, respectively. In addition, the so-called "mark-space" ratio, i.e. the ratio of on signal to off signal is preferably one although other ratios may be used without deleterious effect. Sources of electromagnetic radiation which produce chopped light with different frequencies of chopping or different mark-space ratios are known in the art. The detector 7 determines the time delay (or "correlation delay") between each pulse of light from light source 6 and the corresponding electrical signal detected by detector 7 from transducer 3. The applicant has found that this time delay is a function of the distance, d.

Any method for determining the time delay between each pulse of light and the corresponding electrical signal which provides reproducible results may be used. Preferably, the time delay is measured from the start of each pulse of light to the point at which a maximum in the electrical signal corresponding to the absorption of heat is detected as by detector 7.

Thus reagent 2 may be separated from the transducer surface and a signal may still be detected. Moreover, not only is the signal detectable through an intervening medium capable of transmitting energy to the transducer 3, but different distances, d, may be distinguished (this has been termed "depth profiling") and that the intensity of the signal received is proportional to the concentration of the reagent 2 at the particular distance, d, from the surface of the transducer 3.

In a typical immunoassay, an antibody specific for an antigen of interest is attached to a polymeric support such as a sheet of nitrocellulose, polyvinylchloride or polystyrene. A drop of a sample is laid on the sheet, which is washed after formation of the antibody-antigen complex. Antibody specific for a different site on the antigen is then added, and the sheet is again washed. This second antibody carries a label so that it can be detected with high sensitivity. The amount of second antibody bound to the sheet is proportional to the quantity of antigen in the sample. This assay and other variations on this type of assay are well known, see, for example, "The Immunoassay Handbook, 2nd Ed." David Wild, Ed., Nature Publishing Group, 2001. The device of the present invention may be used in any of these assays.

Figure 2:
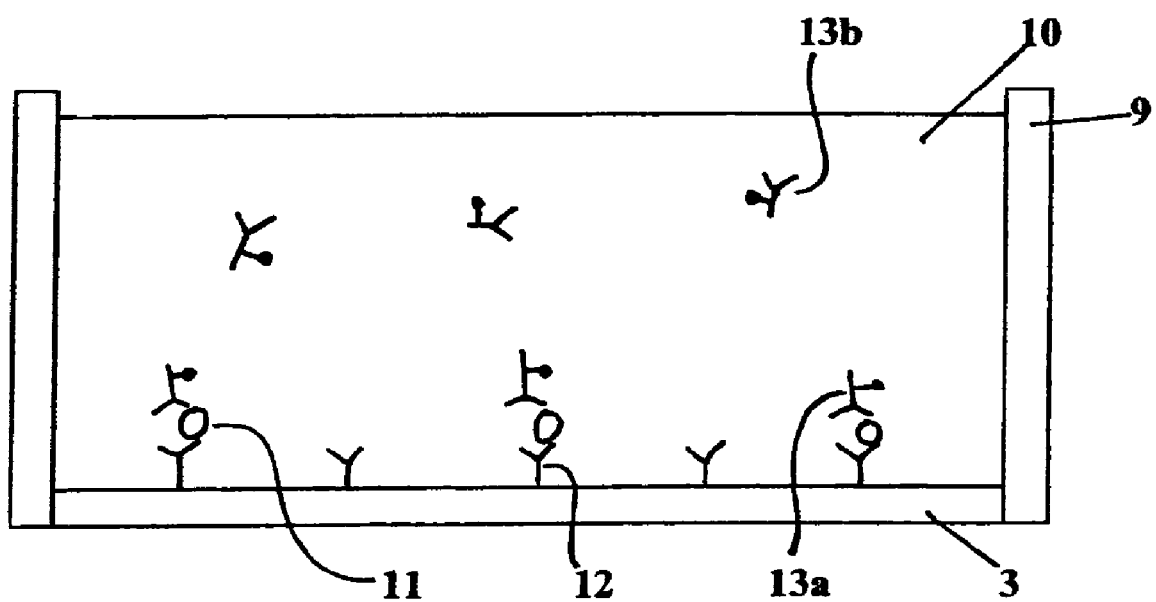
FIG. 2 shows a sandwich immunoassay using the device of the present invention.

FIG. 2 shows a typical capture antibody assay using a piezoelectric or pyroelectric transducer. A device includes a transducer 3 and a well 9 holding a liquid 10 containing an analyte 11 dissolved or suspended therein. The well 9 holds the sample in fluid contact with the transducer 3. The transducer 3 has a number of tethered reagents attached thereto, i.e. antibody 12. The antibody 12 is shown attached to the film in FIG. 2 and this attachment may be via a covalent bond or by non-covalent adsorption onto the surface, such as by hydrogen bonding. Although the antibody is shown as attached to the transducer, any technique for holding the antibody 12 on or proximal to the transducer 3 is applicable. For example, an additional layer may separate the antibody 12 and the transducer 3, such as a silicone polymer layer, or the antibody could be attached to inert particles and the inert particles are then attached to the transducer 3. Alternatively, the antibody 12 could be entrapped within a gel layer which is coated onto the surface of the transducer 3.

In use, the well is filled with liquid 10 (or any fluid) containing an antigen 11. The antigen 11 then binds to antibody 12. Additional labelled antibody 13 is added to the liquid and a so-called "sandwich" complex is formed between the bound antibody 12, the antigen 11 and the labelled antibody 13. An excess of labelled antibody 13 is added so that all of the bound antigen 11 forms a sandwich complex. The sample therefore contains bound labelled antigen 13a and unbound labelled antigen 13b free in solution.

During or following formation of the sandwich complex, the sample is irradiated using a series of pulses of electromagnetic radiation, such as light. The time delay between each pulse and the generation of an electrical signal by the transducer 3 is detected by a detector. The appropriate time delay is selected to measure only the heat generated by the bound labelled antigen 13a. Since the time delay is a function of the distance of the label from the transducer 3, the bound labelled antibody 13a may be distinguished from the unbound labelled antigen 13b. This provides a significant advantage over the conventional sandwich immunoassay in that it removes the need for washing steps. In a conventional sandwich immunoassay, the unbound labelled antibody must be separated from the bound labelled antibody before any measurement is taken since the unbound labelled antigen interferes with the signal generated by the bound labelled antigen. However, on account of the "depth profiling" provided by the present invention, bound and unbound labelled antigen may be distinguished.

The tethered reagent is attached to the transducer 3 and hence is distinct from the labelled reagent which is not tethered to the transducer and is free to diffuse through the liquid.

As a further example of known immunoassays, the present invention may be applied to competitive assays in which the electrical signal detected by the detector is inversely proportional to the presence of an unlabelled antigen in the sample. In this case, it is the amount of the unlabelled antigen in the sample which is of interest.

In a competitive immunoassay, an antibody is attached to the transducer as shown in FIG. 2. A sample containing the antigen is then added. However, rather than adding a labelled antibody, a known amount of labelled antigen is added to the solution. The labelled and unlabelled antigens then compete for binding to the antibodies attached to the transducer 3. The concentration of the bound labelled antigen is then inversely proportional to the concentration of bound unlabelled antigen and hence, since the amount of labelled antigen is known, the amount of unlabelled antigen in the initial solution may be calculated. The same labels specified with reference to the antibodies may also be used with the antigens. In this embodiment, the labelled reagent is therefore a labelled analyte. Many forms of competitive immunoassay are known in the art including those where the antibody in solution is labelled and an antigen is bound to the sensor surface (see, for example, Wild, the Immunoassay Handbook given above).

In assays of the types described above it would be expected that since only the signal at a known distance from the transducer 3 is determined, any other components of the sample which are free in solution or suspension should not interfere with the detection. However, it has been found that suspended particles present in the sample settle and this settling interferes with the reading. This is particularly problematic where the suspended particles absorb radiation strongly at the wavelength of light being used to irradiate the sample. Typically in the art this problem is addressed by carrying out an initial separation of the sample to remove suspended particles, for example to remove red blood cells and other contaminants from a sample of whole blood. However, the present invention avoids the need for a separation step when using a sample of whole blood by a transducer which is in a sufficiently non-horizontal plane that the effects of settling are removed.

Figure 3A:
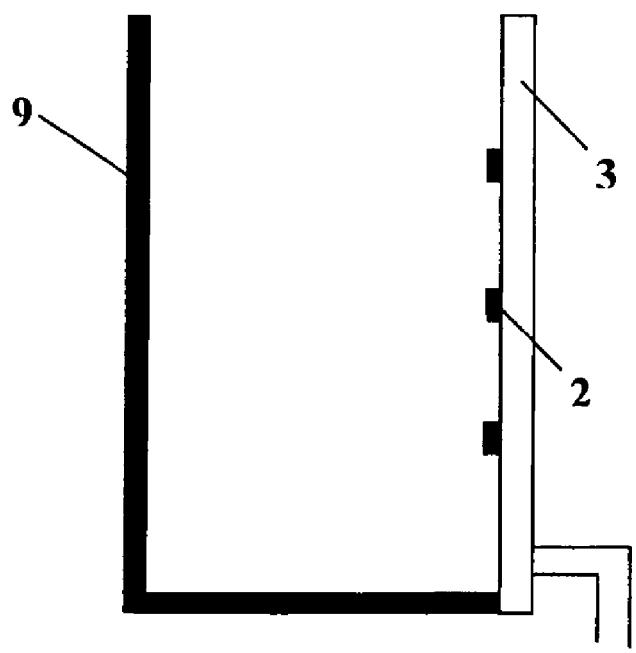
FIG. 3 shows a number of devices having a transducer at an angle of (a) vertical, (b) +15° from vertical, (c) +30° from vertical and (d) −6° from vertical.
Figure 3B:
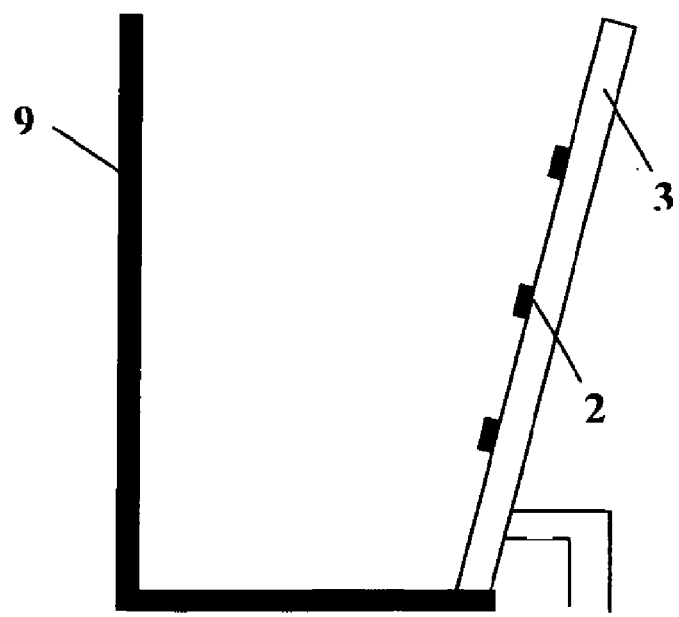
Figure 3C:
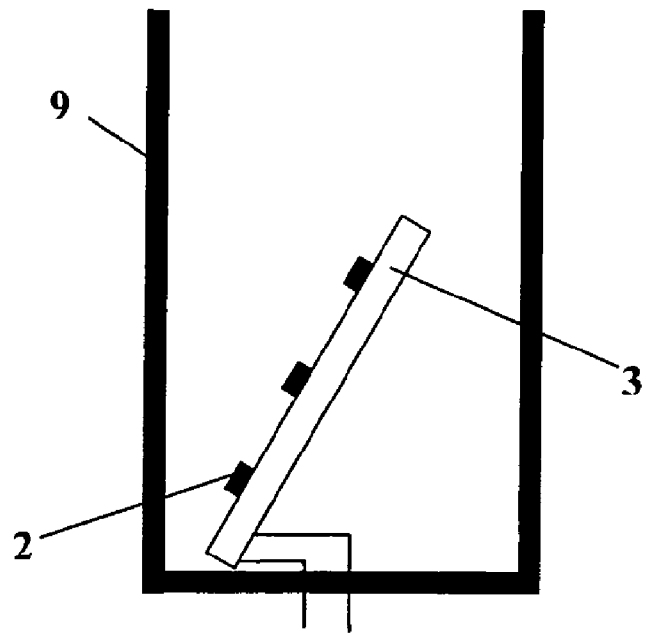
Figure 3D:
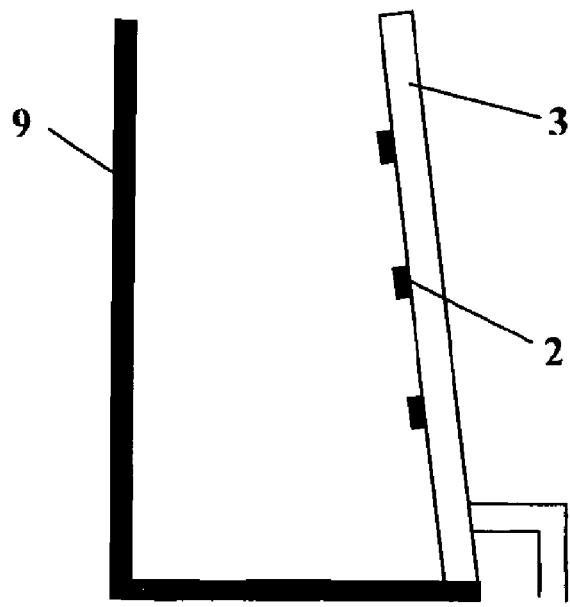

The device of the present invention employs the transducer described hereinabove and may be used to perform the immunoassays described hereinabove, but employs the transducer in a plane which is from +45' to −45° from the vertical. FIG. 3 shows a number of arrangements of the device of the present invention. FIG. 3a shows a device having a transducer 3 integral to the well 9 forming a vertical wall of the well. FIG. 3b shows a device also having a transducer 3 integral to the well 9 in which the transducer is in a plane having an angle of +15° from the vertical. FIG. 3c shows a transducer which is not integral to well but is contained within the well. The transducer is in a plane having an angle of +30° from the vertical. The surface of the transducer is shown having reagents 2 attached thereto. The surface containing the reagents defines the surface of the transducer 3 which interacts with the analyte. This surface defines the angle from the vertical used herein. However, both surfaces of the transducer 3 could be used meaning that the transducer would present both a positive and negative angle from the vertical. FIG. 3d shows a device having a transducer 3 integral to the well 9 in which the transducer is in a plane having an angle of −6° from the vertical.

Although not wishing to be bound by theory, it is believed that there are two effects occurring in the present system. Firstly, the suspended particles and the analyte are free to diffuse through the liquid sample. By diffusion, the analyte will contact the reagent present on the transducer leading to a signal being detected. Secondly, the suspended particles will settle under the force of gravity. By incorporating a transducer in a plane +45° to −45' from the vertical, the effect of settling on the signal may be separated from the effect of diffusion and hence eliminated.

Preferably the transducer is in a plane +30° to −30° from the vertical, more preferably in a plane +15° to −15° from the vertical, more preferably in a plane +5° to −5° from the vertical, more preferably in substantially vertical plane and most preferably vertical.

An apparatus for measuring analyte levels in a blood sample preferably comprises a hand-held portable reader and a disposable device containing the piezoelectric or pyroelectric film. A small sample of blood (about 10 microliters) is obtained and transferred to a chamber within the disposable device. One side of the chamber is made from the piezoelectric or pyroelectric film coated with an antibody capable of binding to the analyte of interest. An additional solution may then be added containing, for example, labelled antibody or a known concentration of labelled antigen as described above. The reaction is allowed to proceed and the disposable device is then inserted into the reader which activates the measurement process. The results of the assay are then indicated on a display on the reader. The disposable device containing the piezoelectric film is then removed and discarded.

The device described herein is not restricted to detecting only one analyte in solution. Since the device provides "depth profiling" different analytes may be detected by employing reagents which selectively bind each analyte being detected wherein the reagents are different distances from the surface of the transducer 3. For example, two analytes may be detected using two reagents, the first reagent being positioned at a first distance from the film and the second reagent being positioned at a second distance from the film. The time delay between each pulse of electromagnetic radiation and the generation of electrical signal will be different for the two analytes bound to the first and second reagents.

As well as providing different depths, multiple tests may be carried out using different types of reagents, e.g. different antibodies, at different parts of the transducer, i.e. specific areas or "spots" on the transducer surface. Alternatively, or in addition, multiple tests may be carried out using reagents/analytes which respond to different wavelengths of electromagnetic radiation.

The reagent generating the heat may be on the surface of the film or the reagent may be at least 5 nm from the surface of the film and, may be no more than 500 μm from the surface of the film.

As well as antibody-antigen reactions, the reagent and analyte may be a first and second nucleic acid where the first and second nucleic acids are complementary, or a reagent containing avidin or derivatives thereof and an analyte containing biotin or derivatives thereof, or vice versa.

The invention claimed is:

1. A device for detecting an analyte in a liquid sample containing suspended particles comprising
   a radiation source adapted to generate electromagnetic radiation,
   a transducer having a pyroelectric or piezoelectric element and electrodes which is capable of transducing a change in energy to an electrical signal,
   at least one reagent on or proximal to the transducer, the reagent being capable of absorbing the electromagnetic radiation to generate energy when in contact with the analyte, a chamber for holding the sample in fluid contact with transducer, and
   a detector which is capable of detecting the electrical signal generated by the transducer,
   wherein the transducer is fixed in a plane from +45° to −45° to the vertical.

2. A device as claimed in claim 1, wherein the transducer is in a plane from +30° to −30° to the vertical.

3. A device as claimed in claim 2, wherein the transducer is in a plane from +15° to −15° to the vertical.

4. A device as claimed in claim 3, wherein the transducer is in a plane from +5° to −5° to the vertical.

5. A device as claimed in claim 4, wherein the transducer is in a substantially vertical plane.

6. A device as claimed in claim 1, wherein the transducer is integral with the chamber.

7. A device as claimed in claim 1, wherein the reagent is adsorbed on to the transducer.

8. A device as claimed in claim 1, wherein the reagent is an antibody and the analyte is an antigen.

9. A device as claimed in claim 1, wherein the radiation source adapted to generate a series of pulses of electromagnetic radiation and the detector is adapted to determine the time delay between each pulse of electromagnetic radiation from the radiation source and the generation of the electric signal.

10. A device as claimed in claim 9, wherein the time delay is at least 1 millisecond.

11. A device as claimed in claim 9, wherein the time delay is no greater than 500 milliseconds.

12. A device as claimed in claim 1, wherein the electromagnetic radiation is light, preferably visible light.

13. A device as claimed in claim 1, wherein the chamber is a well.

14. A device as claimed in claim 10, wherein the time delay is no greater than 500 milliseconds.

* * * * *